United States Patent
Hu

(10) Patent No.: US 11,511,095 B2
(45) Date of Patent: Nov. 29, 2022

(54) PORTABLE TRANSDERMAL ADMINISTRATION PATCH APPARATUS AND PREPARATION METHOD THEREOF

(71) Applicants: CHANGZHOU HUALIAN HEALTH DRESSING LTD., Changzhou (CN); CHANGZHOU HUAJIA MEDICAL DEVICE LTD., Changzhou (CN)

(72) Inventor: Longsheng Hu, Changzhou (CN)

(73) Assignees: CHANGZHOU HUAJIA MEDICAL DEVICE LTD.; CHANGZHOU HUALIAN HEALTH DRESSING LTD.

(*) Notice: Subject to any disclaimer, the term of this patent is extended or adjusted under 35 U.S.C. 154(b) by 780 days.

(21) Appl. No.: 16/478,673

(22) PCT Filed: Jan. 17, 2018

(86) PCT No.: PCT/CN2018/072920
§ 371 (c)(1),
(2) Date: Jul. 17, 2019

(87) PCT Pub. No.: WO2018/133786
PCT Pub. Date: Jul. 26, 2018

(65) Prior Publication Data
US 2019/0381295 A1 Dec. 19, 2019

(30) Foreign Application Priority Data
Jan. 18, 2017 (CN) .......................... 201710037615.5
May 26, 2017 (CN) .......................... 201710382314.6

(51) Int. Cl.
*A61M 35/00* (2006.01)
*A61F 13/02* (2006.01)
(Continued)

(52) U.S. Cl.
CPC ......... *A61M 35/10* (2019.05); *A61F 13/0283* (2013.01); *A61K 9/06* (2013.01);
(Continued)

(58) Field of Classification Search
CPC .......... A61M 35/10; A61M 2205/3592; A61M 37/00; A61M 2205/3584;
(Continued)

(56) References Cited

U.S. PATENT DOCUMENTS 5,328,453 A * 7/1994 Sibalis ................. A61N 1/0448
604/20
6,018,680 A * 1/2000 Flower ................. A61N 1/0428
604/20

(Continued)

FOREIGN PATENT DOCUMENTS

CN 1607970 A 4/2005
CN 103826696 A 5/2014
(Continued)

OTHER PUBLICATIONS

ISR_for_International_Application_No._PCT/CN2018/07290.
(Continued)

*Primary Examiner* — Andrew J Mensh
(74) *Attorney, Agent, or Firm* — Levenfeld Pearlstein, LLC

(57) ABSTRACT

A portable transdermal administration patch apparatus comprises a communication control device and a pharmaceutical device which is fixed to and arranged at a lower end of the communication control device and electrically connected to the communication control device. The communication control device is formed of a micro-battery, a wireless control device and a micro-controller which are electrically connected. The preparation of the patch apparatus is achieved by: the preparation of medicinal patches and non-medicinal (Continued)

patches, the mounting of electrodes, interfacing with a micro-controller, and the communication control system, and starting administration. The transdermal apparatus is wearable and can be remotely controlled, and is convenient for administration, in particular, for the situations of daily administration for elderly patients with chronic illness and when there are a larger number of admitted inpatients, where a nurse can pre-set the administration time and dose, thus saving time and efforts of medical staff.

9 Claims, 2 Drawing Sheets

(51) Int. Cl.
| | |
|---|---|
| *A61K 9/70* | (2006.01) |
| *A61K 9/06* | (2006.01) |
| *A61K 9/127* | (2006.01) |
| *A61K 31/4178* | (2006.01) |
| *A61K 31/554* | (2006.01) |
| *A61K 47/12* | (2006.01) |
| *A61K 47/36* | (2006.01) |
| *A61K 47/38* | (2006.01) |

(52) U.S. Cl.
CPC ............ *A61K 9/127* (2013.01); *A61K 9/7084* (2013.01); *A61K 31/4178* (2013.01); *A61K 31/554* (2013.01); *A61K 47/12* (2013.01); *A61K 47/36* (2013.01); *A61K 47/38* (2013.01); *A61F 2013/0296* (2013.01); *A61M 2205/3584* (2013.01); *A61M 2205/3592* (2013.01); *A61M 2205/50* (2013.01); *A61M 2205/8206* (2013.01); *A61M 2207/00* (2013.01)

(58) Field of Classification Search
CPC ...... A61M 2037/0007; A61M 2207/00; A61M 2205/50; A61M 2205/8206; A61K 31/4178; A61K 9/127; A61K 9/7084; A61K 9/06; A61K 31/554; A61K 47/38; A61K 47/36; A61K 47/12; A61F 13/0283; A61F 2013/0296; A61N 1/303
USPC .......................................................... 604/307
See application file for complete search history.

(56) References Cited

U.S. PATENT DOCUMENTS

| | | | | |
|---|---|---|---|---|
| 9,014,779 | B2* | 4/2015 | Zdeblick | ................ A61B 5/725 600/382 |
| 9,095,503 | B2* | 8/2015 | Imran | ................ A61K 31/4178 |
| 2013/0274576 | A1* | 10/2013 | Amirouche | ......... A61M 5/1408 604/151 |

FOREIGN PATENT DOCUMENTS

| | | |
|---|---|---|
| CN | 204335849 U | 5/2015 |
| CN | 106110490 A | 11/2016 |
| CN | 107029343 A | 8/2017 |

OTHER PUBLICATIONS

Written_Opinion_for_International_Application_No._PCT/CN2018/072920.
CN 107029343 A—Espacenet English Abstract.
CN 106110490 A—Espacenet English Abstract.
CN 204335849 U—Espacenet English Abstract.
CN 1607970 A—Espacenet English Abstract.
CN 103826696 A—Espacenet English Abstract.

* cited by examiner

PORTABLE TRANSDERMAL ADMINISTRATION PATCH APPARATUS AND PREPARATION METHOD THEREOF

CROSS-REFERENCE TO RELATED APPLICATIONS

The present application is a national phase of Ser. No. PCT/CN2018/072920 filed Jan. 17, 2018, the entire contents of which are incorporated herein by reference, and which claims priority to and the benefit of Chinese Patent Application No. CN 201710037615.5 filed on Jan. 18, 2017 and Chinese Patent Application No. CN 201710382314.6, filed on May 26, 2017.

BACKGROUND OF THE INVENTION

1. Field of the Invention

The invention relates to the field of technology of medical devices, and more particularly, to a portable transdermal administration patch apparatus and a preparation method thereof.

2. Description of the Related Art

Currently, most drugs are administered orally or in the form of injections. Dosage formulations for oral administration include tablets, capsules and liquids. However, since gastrointestinal absorption and hepatic first pass effect may occur when the drug is administered orally, the bioavailability of the drugs has been reduced before they reach a site of action, and side effects may occur. Some other drugs cannot be administered orally, such as peptides and protein-related drugs. Another common route of administration is injection that allows the drug to penetrate into a biological barrier, including subcutaneous injection and intravenous injection. Although such method was proved to be fast and effective, there are some disadvantages, such injection hurt, skin injury and dermatorrhagia of the injection site, sometimes even scytitis. In addition, such route of administration needs to be taken by health professionals, therefore, it is not suitable for patients who needs to be administered continuously for a long period of time in a control manner, reducing compliance of the patient.

As the third route of administration, the transdermal administration system refers to a route of administration in which drugs are delivered across the skin and capillary for systemic blood circulation, then an effective blood concentration is reached, and finally pharmaceutical effect can be achieved. In this way, the first pass effect of the oral administration may be avoided, and the pharmaceutical effect and the bioavailability are improved as well; a durable, constant and controllable blood concentration is obtainable, thereby reducing side effects and not causing hurt as injection does, and increasing the compliance of the patient. The transdermal administration is safe and controllable, and it represents a new route of non-invasive administration, having a broad market prospect. However, the transdermal administration needs to be delivered into the skin. Since the skin is the largest organ of human beings, protecting the human body from external infections and having a dense structure, drug molecules cannot readily penetrate into the skin, and the dose that is delivered into the skin is quite limited. At present, the number of systemic drugs, that is allowed to delivered into the skin, is less than 50. The available transdermal drugs features small molecule and low concentration, the presence of the stratum corneum barrier makes it difficult for the most drugs to pass through or reach an effective concentration and an effective rate. The key for the transdermal administration is to facilitate the perpetration of the drugs, allowing the drug to be delivered into the skin and be absorbed into the capillary. In order to promote transdermal absorption of drugs, researchers around the world have developed various physical and chemical methods and a combination thereof. The physical method comprises: iontophoresis, ultrasonic penetration, high pressure gas flow, exothermic promotion, laser energy promotion, etc.; and the chemical method comprises: penetration enhancers, prodrugs, chemical modifications, protease inhibitors, and penetration enhancers with iontophoresis, ultrasonic penetration with penetration enhancers, and even iontophoresis with ultrasonic penetration. However, the existing chemical methods will pose damage to the skin. And although the physical method, such as iontophoresis and ultrasonic penetration, is effective, it is inconvenient for patients to use at home.

SUMMARY OF THE INVENTION

It is an object of the present invention to overcome disadvantages of the prior art, and to provide a new type of integrated, wearable portable transdermal administration patch apparatus through which the administration can be remotely controlled, and a preparation method thereof.

In order to solve the above-mentioned technical problems, the present invention adopts the following technical solutions:

A portable transdermal administration patch apparatus, comprising: a communication control device and a pharmaceutical device, wherein the pharmaceutical device is fixed to and arranged at a lower end of the communication control device; the communication control device and the pharmaceutical device are electrically connected; the communication control device is formed of a micro-battery, a wireless control device and a micro-controller a; and the micro-battery, the wireless control device and the micro-controller a are electrically connected;

the pharmaceutical device is formed of a micro-controller b, an apparatus switch and a patch body, wherein the micro-controller b and the apparatus switch are electrically connected, the patch body is fixed to and arranged at a bottom end of the micro-controller b, and the patch body is integrally formed with the micro-controller b.

Furthermore, the patch body comprises medicinal patches and non-medicinal patches, the medicinal patches are spaced from the non-medicinal patches by a distance in the range of 0.01 to 5 mm, more preferably, a distance in the range of 0.1 to 2.0 mm.

Furthermore, the wireless control device comprises a short-range wireless control device and a long-range wireless control device; the short-range wireless control device is selected from the group consisting of a WIFI and a Bluetooth chip.

Furthermore, the long-range wireless control device consists of a controller c and a GPRS chip module.

It is a further object of the present invention to disclose a preparation method for the portable transdermal administration patch apparatus, wherein the preparation of the portable transdermal administration patch apparatus is achieved by means of the following steps: the preparation of the medicinal patches, the preparation of the non-medicinal patches, the mounting of electrodes, interfacing with the micro-controller b, interfacing with a communication control system, and starting administration; and the detailed steps are as follows:

(1) the preparation of the medicinal patches: an aqueous solution containing medicine prepared is injected into a middle portion of a medicinal cotton, wherein 0.2 mm of an outer periphery of the cotton is attached to a medicinal adhesive tape, and the middle portion of the cotton is attached to a piece of protective paper, so as to complete the preparation of the medicinal patches;

(2) the preparation of the non-medicinal patches: water, emulsion, gel, lipids, or microspheres containing no medicine is injected into the middle portion of the medicinal cotton, the outer periphery of the cotton having a width of 0.2 mm is attached to a medicinal adhesive tape, the middle portion of the cotton, having a surface area of 1.0-1.5 cm$^2$ is attached to a piece of protective paper, and the protective paper is attached to the medicinal adhesive tape, so as to complete the preparation of the non-medicinal patches;

(3) the mounting of electrodes: an insertion of a metal electrode and a corresponding meal salt electrode is conducted based on the charging characteristics of medicine in the medicinal patches, wherein it is preferable that the metal is Ag, and that the metal salt is AgCI;

(4) interfacing with the micro-controller b: a portion of the patch with an Ag electrode interfaces with a positive electrode of the micro-controller b, and a portion of the patch with an AgCI electrode interfaces with a negative electrode of the micro-controller b;

(5) interfacing with a communication control system: the communication control system is electrically connected to the micro-controller b; and (6) starting administration: set electric quantity, current and conduction time in a display screen of the micro-controller b, press the apparatus switch and start administration, and the current is in the range of 0.01 to 2 mA, preferably in the range of 0.1 to 0.5 mA.

Furthermore, during the preparation of the medicinal patches, medicinal liquid is prepared in the following steps: four materials, namely, carmellose, water, citrate, and ondansetron, are mixed at a weight ratio of 1:98.49:0.01:0.5, so as to form a colloidal aqueous solution of 3000 CPS, and the colloidal aqueous solution has a pH of 3.6.

Furthermore, during the preparation of the medicinal patches, medicinal liquid is prepared in the following steps: a non-ionized macromolecule drug is encapsulated by means of a carrier, the encapsulated non-ionized macromolecule drug is dissolved in an aqueous solution to form a suspension or gel, and a weight ratio of the carrier to the non-ionized macromolecule drug is 50-70:30-60, more preferably 65:35.

Furthermore, the carrier is selected from one of the group consisting of: chitosan lactate, other macromolecule ionic surfactants and liposomes.

Furthermore, during the preparation of the medicinal patches, medicinal liquid is prepared in the following steps: water and diltiazem hydrochloride are mixed at a weight ratio of 98:2, so as to form an aqueous solution, and the aqueous solution has a pH of 5.5.

Furthermore, a method for preparation of the non-medicinal patches is as follows: carmellose and water are mixed at a weight ratio of 2:98, so as to form a colloidal aqueous solution of 10000 CPS, the colloidal aqueous solution is injected into the middle portion of the medicinal cotton, the outer periphery of the cotton having a width of 0.2-0.5 mm is attached to the medicinal adhesive tape, the middle portion of the cotton, having a surface area of 1.0-1.5 m$^2$ is attached to a piece of protective paper, and the protective paper is then attached to the medicinal adhesive tape, so as to complete the preparation of the non-medicinal patches.

The present invention has the following advantageous, effects:

(1) The transdermal apparatus according to the present invention is wearable and can be remotely controlled, and is convenient for administration, in particular, for the situations of daily administration for elderly patients with chronic diseases and when there are a larger number of admitted inpatients, where a nurse can pre-programme the administration time and pre-set dose according to the prescription requirements of doctors, so as to administer patients with the medicine at a pre-programmed time and with a pre-set dose, thus saving time and efforts of medical staff.

(2) Administration may be done safely by using the portable transdermal administration patch apparatus according to the present invention without damaging the skin of the patients; the administration process is painless; and drug specifies for transdermal administration are increased, and bioavailability of such drugs is improved.

(3) the dose for transdermal administration can be accurately controlled, and can be effectively applied to transdermal systemic administration and transdermal local administration.

BRIEF DESCRIPTION OF THE DRAWINGS

The accompanying drawings, together with the specification, illustrate exemplary embodiments of the present disclosure, and, together with the description, serve to explain the principles of the present invention.

DETAILED DESCRIPTION

Figure 1:
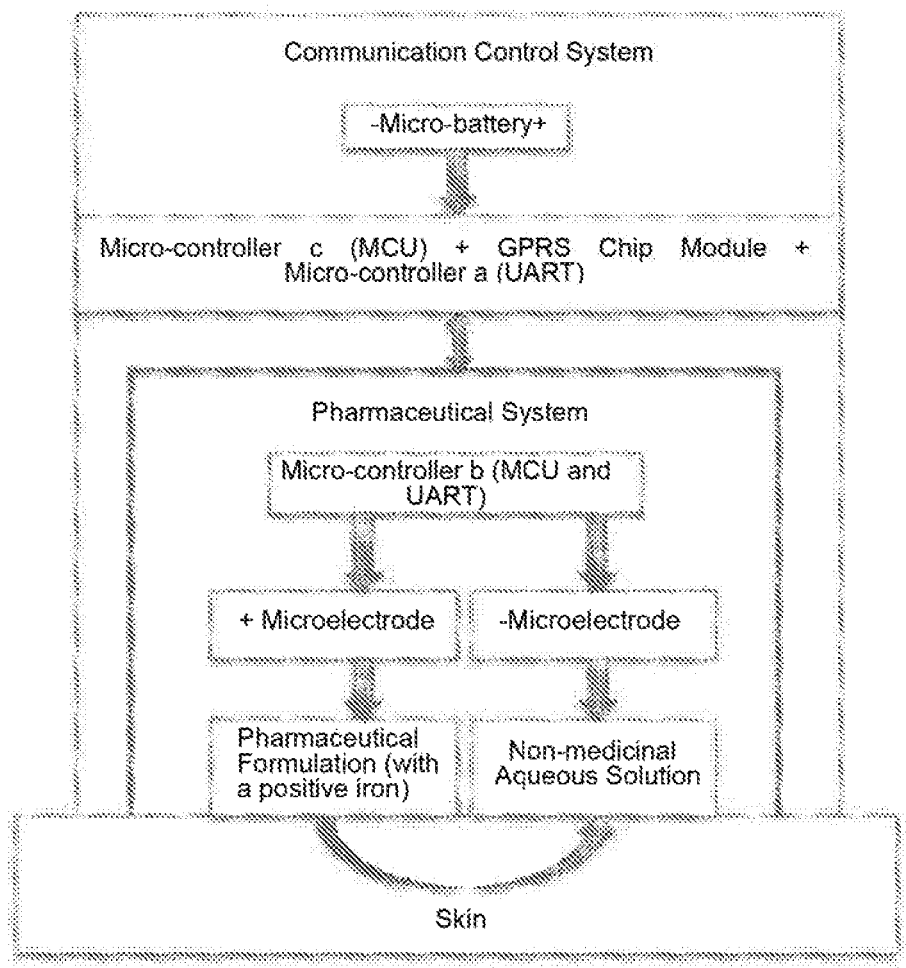
FIG. 1 is a schematic view showing an overall structure of a long-range administration patch apparatus according to the present invention.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, certain exemplary embodiments according to the present disclosure will be described with reference to the accompanying drawings.

Figure 2:
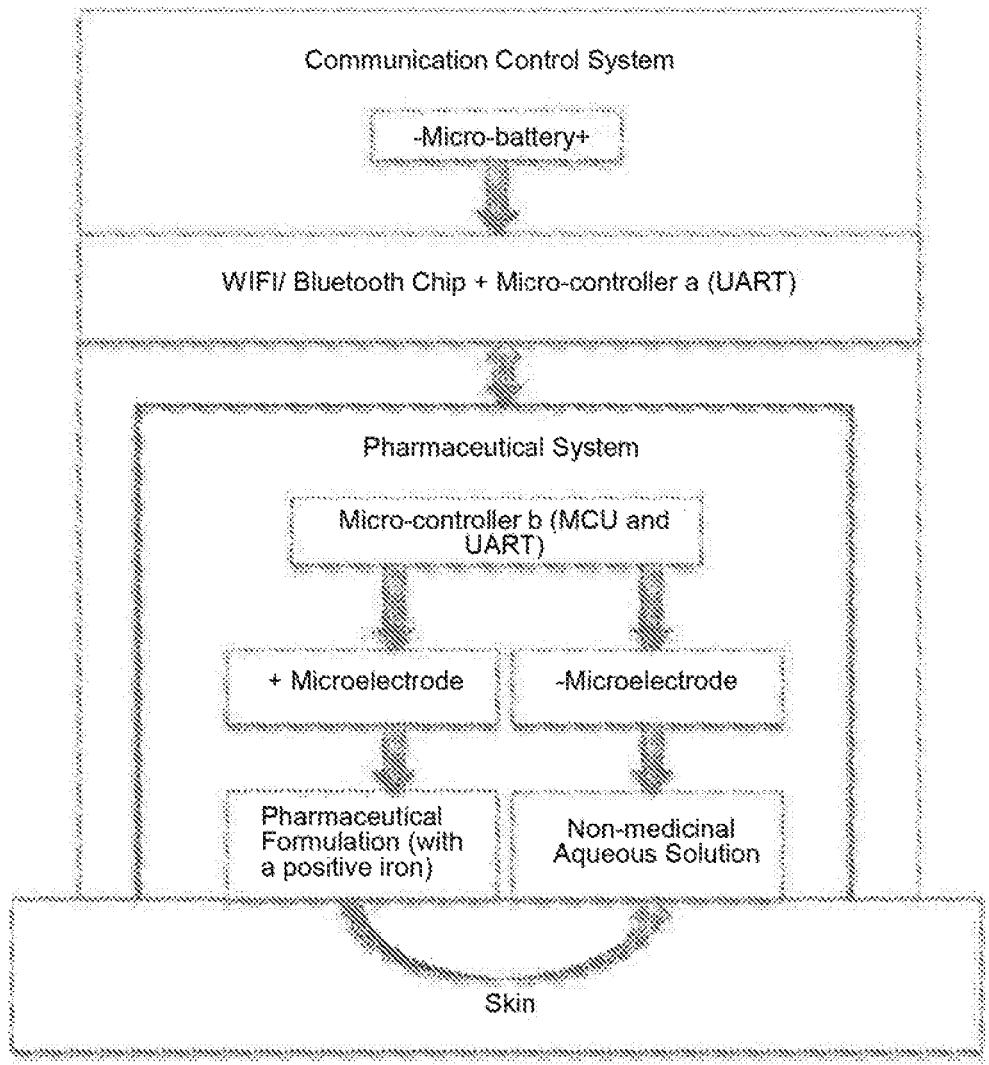
FIG. 2 is a schematic view showing an overall structure of a short-range administration patch apparatus according to the present invention.

As shown in FIGS. 1 and 2, A portable transdermal administration patch apparatus, comprising: a communication control device and a pharmaceutical device, wherein the pharmaceutical device is fixed to and arranged at a lower end of the communication control device; the communication control device and the pharmaceutical device are electrically connected; the communication control device is formed of a micro-battery, a wireless control device and a micro-controller a; and the micro-battery, the wireless control device and the micro-controller a are electrically connected, and it is preferable that the micro-battery is a button cell or a paper battery;

the pharmaceutical device is formed of a micro-controller b, an apparatus switch and a patch body, wherein the micro-controller b and the apparatus switch are electrically connected, the patch body is fixed to and arranged at a bottom end of the micro-controller b, and the patch body is integrally formed with the micro-controller b.

The patch body comprises medicinal patches and non-medicinal patches, the medicinal patches are spaced from the non-medicinal patches by a distance in the range of 0.01 to 5 mm, more preferably, a distance in the range of 0.1 to 2.0 mm.

The wireless control device comprises a short-range wireless control device and a long-range wireless control device; the short-range wireless control device is selected from the group consisting of a WIFI and a Bluetooth chip.

The long-range wireless control device consists of a controller c and a GPRS chip module.

A preparation method for the portable transdermal administration patch apparatus, wherein the preparation of the portable transdermal administration patch apparatus is achieved by means of the following steps: the preparation of the medicinal patches, the preparation of the non-medicinal patches, the mounting of electrodes, interfacing with the micro-controller b, interfacing with a communication control system, and starting administration; and the detailed steps are as follows:

(1) the preparation of the medicinal patches: an aqueous solution containing medicine prepared is injected into a middle portion of a medicinal cotton, wherein 0.2 mm of an outer periphery of the cotton is attached to a medicinal adhesive tape, and the middle portion of the cotton is attached to a piece of protective paper, so as to complete the preparation of the medicinal patches;

(2) the preparation of the non-medicinal patches: water, emulsion, gel, lipids, or microspheres containing no medicine is injected into the middle portion of the medicinal cotton, the outer periphery of the cotton having a width of 0.2 mm is attached to a medicinal adhesive tape, the middle portion of the cotton, having a surface area of 1.0-1.5 cm$^2$ is attached to a piece of protective paper, and the protective paper is attached to the medicinal adhesive tape, so as to complete the preparation of the non-medicinal patches;

(3) the mounting of electrodes: an insertion of a metal electrode and a corresponding meal salt electrode is conducted based on the charging characteristics of medicine in the medicinal patches, wherein it is preferable that the metal is Ag, and that the metal salt is AgCI;

(4) interfacing with the micro-controller b: a portion of the patch with an Ag electrode interfaces with a positive electrode of the micro-controller b, and a portion of the patch with an AgCI electrode interfaces with a negative electrode of the micro-controller b;

(5) interfacing with a communication control system: the communication control system is electrically connected to the micro-controller b; and (6) starting administration: set electric quantity, current and conduction time in a display screen of the micro-controller b, press the apparatus switch and start administration, and the current is in the range of 0.01 to 2 mA, preferably in the range of 0.1 to 0.5 mA.

Feasibly, during the preparation of the medicinal patches, medicinal liquid is prepared in the following steps: four materials, namely, carmellose, water, citrate, and ondansetron, are mixed at a weight ratio of 1:98.49:0.01:0.5, so as to form a colloidal aqueous solution of 3000 CPS, and the colloidal aqueous solution has a pH of 3.6.

Feasibly, during the preparation of the medicinal patches, medicinal liquid is prepared in the following steps: a non-ionized macromolecule drug is encapsulated by means of a carrier, the encapsulated non-ionized macromolecule drug is dissolved in an aqueous solution to form a suspension or gel, and a weight ratio of the carrier to the non-ionized macromolecule drug is 50-70:30-60, more preferably 65:35; and the carrier is selected from one of the group consisting of: chitosan lactate, other macromolecule ionic surfactants and liposomes.

Feasibly, during the preparation of the medicinal patches, medicinal liquid is prepared in the following steps: water and diltiazem hydrochloride are mixed at a weight ratio of 98:2, so as to form an aqueous solution, and the aqueous solution has a pH of 5.5.

a method for preparation of the non-medicinal patches is as follows: carmellose and water are mixed at a weight ratio of 2:98, so as to form a colloidal aqueous solution of 10000 CPS, the colloidal aqueous solution is injected into the middle portion of the medicinal cotton, the outer periphery of the cotton having a width of 0.2-0.5 mm is attached to the medicinal adhesive tape, the middle portion of the cotton, having a surface area of 1.0-1.5 cm$^2$ is attached to a piece of protective paper, and the protective paper is then attached to the medicinal adhesive tape, so as to complete the preparation of the non-medicinal patches.

Example 1

Simulation experiment of in vitro transdermal drug delivery in pig skin:

(1) pig skin with a thickness of 300-500 μm and an area of 1.0 cm$^2$ was selected and placed between the Franz diffusion cell supply cell and the Franz diffusion cell receiving cell. An inner side of the pig skin was oriented toward the supply cell, and then the patch apparatus was placed in the supply cell and was attached to the epidermis of the pig skin. The receiving cell was filled with phosphate buffered saline to simulate blood circulation, and the temperature in the receiving cell was maintained at 37° C. to simulate human body temperature.

(2) Set the electric quantity: 0.1 mA, the conduction time is 24 hours as desired. Press a power switch of the patch apparatus.

(3) After 24 hours, the sample was retrieved from the receiving cell, and drugs were analyzed by a high-pressure liquid phase analyzer and the result was recorded.

Table 1 below shows a comparison table for the analysis record of ondansetron, an anti-vomiting drug, and a traditional patch transdermal administration:

TABLE 1

| Quantity of electric charge (mA * hour) | Administration speed μg/(cm$^2$ * h)) | Administration dosage (μg/cm$^2$ skin area contacted by the drug formulation) |
|---|---|---|
| 0 (traditional patch) | 0.1 | 1.2 |
| 2.4 (this method) | 1.8 | 53.2 |

From the Table 1, it can be seen that this method can greatly increase the administration speed and dosage by using the electric power within the same 24 hours.

Table 2 below shows a comparison table for the analysis record of diltiazem hydrochloride, an hypotensive drug, and a traditional patch transdermal administration:

TABLE 2

| Quantity of electric charge (mA * hour) | Administration speed μg/(cm$^2$ * h)) | Administration dosage (μg/cm$^2$ skin area contacted by the drug formulation) |
|---|---|---|
| 0 (traditional patch) | 0.9 | 17.9 |
| 2.4 (this apparatus) | 10.3 | 310.1 |

From Tables 1 and 2, it can be seen that the administration speed and dosage can be greatly increased by using the method according to the present invention.

The transdermal apparatus according to the present invention is wearable and can be remotely controlled, and is convenient for administration, in particular, for the situations of daily administration for elderly patients with chronic illness and when there are a larger number of admitted inpatients, where a nurse can pre-set the administration time and dose according to the prescription requirements of doctors, so as to administer patients with the medicine at a fixed time and with a fixed dose, thus saving time and efforts of medical staff.

Administration may be done safely by using the portable transdermal administration patch apparatus according to the present invention without damaging the skin of the patients; the administration process is painless; and drug specifies for transdermal administration are increased, and bioavailability of such drugs is improved.

The dose for transdermal administration can be accurately controlled, and can be effectively applied to transdermal systemic administration and transdermal local administration.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A preparation method fora portable transdermal administration patch apparatus, the portable transdermal administration patch apparatus, comprising
a communication control device and a pharmaceutical device, wherein the pharmaceutical device is fixed to and arranged at a lower end of the communication control device, wherein the communication control device and the pharmaceutical device are electrically connected, wherein the communication control device is formed of a micro-battery, a wireless control device and a first micro-controller, the micro-battery, the wireless control device and the first micro-controller being electrically connected,
wherein the pharmaceutical device is formed of second micro-controller, an apparatus switch and a patch body, wherein the second micro-controller and the apparatus switch are electrically connected, wherein the patch body is fixed to and arranged at a bottom end of the second micro-controller, and wherein the patch body is integrally formed with second the micro-controller,
wherein the patch body comprises medicinal patches and non-medicinal patches, the medicinal patches being spaced from the non-medicinal patches,
wherein the preparation of the portable transdermal administration patch apparatus comprises the following steps:
the preparation of the medicinal patches, the preparation of the non-medicinal patches, the mounting of electrodes, interfacing with the second micro-controller, interfacing with a communication control system, and starting administration; and the detailed steps are as follows:
(1) the preparation of the medicinal patches: an aqueous solution containing medicine prepared is injected into a middle portion of a medicinal cotton, wherein 0.2 mm of an outer periphery of the cotton is attached to a medicinal adhesive tape, and the middle portion of the cotton is attached to a piece of protective paper, so as to complete the preparation of the medicinal patches;
(2) the preparation of the non-medicinal patches: water, emulsion, gel, lipids, or microspheres containing no medicine is injected into the middle portion of the medicinal cotton, the outer periphery of the cotton having a width of 0.2 mm is attached to a medicinal adhesive tape, the middle portion of the cotton, having a surface area of 1.0-1.5 cm$^2$ is attached to a piece of protective paper, and the protective paper is attached to the medicinal adhesive tape, so as to complete the preparation of the non-medicinal patches;
(3) the mounting of electrodes: an insertion of a metal electrode and a corresponding metal salt electrode is conducted based on the charging characteristics of medicine in the medicinal patches, wherein the metal is Ag, and the metal salt is AgCl;
(4) interfacing with the second micro-controller: a portion of the patch with an Ag electrode interfaces with a positive electrode of the second micro-controller, and a portion of the patch with an AgCl electrode interfaces with a negative electrode of the second micro-controller;
(5) interfacing with a communication control system: the communication control system is electrically connected to the second micro-controller; and
(6) starting administration: set an electric quantity, a current and a conduction time in a display screen of the second micro-controller, press the apparatus switch and start administration, and the current is in the range of 0.01 to 2 mA.

2. The preparation method for the portable transdermal administration patch apparatus according to claim 1, wherein during the preparation of the medicinal patches, medicine containing liquid is prepared in the following steps: four materials, namely, carmellose, water, citrate, and ondansetron, are mixed at a weight ratio of 1:98.49:0.01:0.5, so as to form a colloidal aqueous solution of 3000 CPS, and the colloidal aqueous solution has a pH of 3.6.

3. The preparation method for the portable transdermal administration patch apparatus according to claim 1, wherein during the preparation of the medicinal patches, medicinal liquid is prepared in the following steps: a non-ionized macromolecule drug is encapsulated by means of a carrier, the encapsulated non-ionized macromolecule drug is dissolved in an aqueous solution to form a suspension or gel, and a weight ratio of the carrier to the non-ionized macromolecule drug is 50-70:30-60.

4. The preparation method for the portable transdermal administration patch apparatus according to claim 3, wherein the carrier is selected from one of the group consisting of: chitosan lactate, other macromolecule ionic surfactants and liposomes.

5. The preparation method for the portable transdermal administration patch apparatus according to claim 1, wherein during the preparation of the medicinal patches, medicinal liquid is prepared in the following steps: water and diltiazem hydrochloride are mixed at a weight ratio of 98:2, so as to form an aqueous solution, and the aqueous solution has a pH of 5.5.

6. The preparation method for the portable transdermal administration patch apparatus according to claim 1, wherein a method for preparation of the non-medicinal patches is as follows: carmellose and water are mixed at a weight ratio of 2:98, so as to form a colloidal aqueous solution of 10000 CPS, the colloidal aqueous solution is injected into the middle portion of the medicinal cotton, the outer periphery of the cotton having a width of 0.2-0.5 mm is attached to the medicinal adhesive tape, the middle portion of the cotton, having a surface area of 1.0-1.5 $cm^2$ is attached to a piece of protective paper, and the protective paper is then attached to the medicinal adhesive tape, so as to complete the preparation of the non-medicinal patches.

7. The preparation method for the portable transdermal administration patch apparatus according to claim 1, wherein the medicinal patches are spaced from the non-medicinal patches by a distance in the range of 0.01 to 5 mm.

8. The preparation method for the portable transdermal administration patch apparatus according to claim 1, wherein the wireless control device comprises a short-range wireless control device and a long-range wireless control device; the short-range wireless control device is selected a WIFI or a Bluetooth chip.

9. The preparation method for the portable transdermal administration patch apparatus according to claim 8, wherein the long-range wireless control device consists of a third controller and a GPRS chip module.

* * * * *